United States Patent [19]

Schlüter et al.

[11] Patent Number: 5,457,092
[45] Date of Patent: Oct. 10, 1995

[54] METHODS OF PROMOTING BONE GROWTH IN MAMMALS COMPRISING ADMINISTRATION OF MODIFIED PARATHYROID HORMONE

[75] Inventors: Klaus-Dieter Schlüter; Hubert Mayer; Edgar Wingender, all of Braunschweig, Germany

[73] Assignee: Gesellschaft fur Biotechnologische Forschung mbH (GBF), Braunschweig, Germany

[21] Appl. No.: 120,248

[22] Filed: Sep. 13, 1993

Related U.S. Application Data

[63] Continuation-in-part of Ser. No. 6,702, Jan. 21, 1993, abandoned, which is a continuation of Ser. No. 225,344, Jul. 28, 1988, abandoned.

[30] Foreign Application Priority Data

Jul. 30, 1987 [DE] Germany .......................... 37 25 319.0

[51] Int. Cl.⁶ .......................... C07K 7/00; C07K 14/635; A61K 38/00; A61K 38/29

[52] U.S. Cl. .......................... 514/12; 530/350; 530/324; 530/399; 435/69.7; 435/69.4; 514/13

[58] Field of Search .......................... 514/12; 530/350, 530/324, 399; 435/69.7, 69.4

OTHER PUBLICATIONS

Schluter et al. 1989. J. Biol. Chem. 264:11087–11092.
Somjen et al. 1990. Biochem. J. 272:781–785.
Slovik et al. 1986. J. Bone Min. Res. 1:377–381.
Somjen et al. 1991, Biochem. J. 277:863–868.
Potts et al. 1982. Adv. Prot. Chem. 35:323–389.

*Primary Examiner*—Garnette D. Draper
*Assistant Examiner*—Elizabeth C. Kemmerer
*Attorney, Agent, or Firm*—Kane, Dalsimer, Sullivan, Kurucz, Levy, Eisele and Richard

[57] ABSTRACT pPTH, bPTH or hPTH is modified by deletions from the natural C- and/or N-terminus. The modified compounds are useful active ingredients in therapeutic compositions. The therapeutic compositions do not stimulate renal adenylate cyclase but, rather, effect chondrocyte proliferation, that is to say, they exhibit a mitogenic and bone-specific effect.

5 Claims, 12 Drawing Sheets

METHODS OF PROMOTING BONE GROWTH IN MAMMALS COMPRISING ADMINISTRATION OF MODIFIED PARATHYROID HORMONE

CROSS REFERENCE TO RELATED APPLICATIONS

This application is a Continuation-In-Part of U.S. application Ser. No. 08/006,702 filed on Jan. 21, 1993, now abandoned, which was a Continuation of U.S. patent application Ser. No. 07/225,344 filed on Jul. 28, 1988, and now abandoned.

BACKGROUND OF THE INVENTION

1. Field of the Invention

The invention relates to parathyroid hormone preparations.

2. Brief Description of Related Art

Parathormone (parathyroid hormone), or PTH, a regulatory hormone of calcium homeostasis, stimulates a number of enzymes. Among them are ornithine decarboxylase and adenylate cyclase. The target organs for PTH are the kidneys, on the one hand, and the bones on the other hand. In the kidneys, the hormone promotes the resorption of calcium and in the bones PTH cooperates in the mobilization of calcium as well as inducing incorporation of calcium.

J. Cell. Biol., 24 (1966) 316–323 (I; Borle & Neumann) describes a growth-promoting effect of PTH on Hela cells in-vitro. Biochem. Biophys. Res. Comm., 66 (1975) 188–194 (2; Morgan et al.) describes such an effect on T-lymphocytes, and Biochem. Biophys. Res. Comm., 129 (1985) 918–925 (3; van der Plas et al.) on osteoblasts from chickens when the osteoblasts were kept in secondary culture. Endocrinology, 118 (1986) 2445–2449 (4; M. Donald et al.) describes such an effect on bone cells. Endocrinology, 110 (1982) 506–512 (5; Tam et al.) describes an increased rate of in-vivo bone growth after the administration of PTH. Endocro Japan, 27 (1980) 349–356 (6; Kawashima et al.) and Calcif. Tissue Int., 35 (1983) 526–532 (7; Burch & Lebovitz) describe a stimulation by PTH of the proliferation of chicken embryo cartilage organ cultures in-vitro and Calcifo Tissue Int., 38 (1986) 155–162 (8; Lewinson & Silbermann) in mouse embryo cartilage organ cultures. In each of the above-mentioned studies, there was used PTH or a PTH fragment that simultaneously resulted in a stimulation of adenylate cyclase in renal cortex membranes, so that, when using this substance as a material for promoting bone growth in-vivo, influence on renal function must also be taken into account.

It is also known that a deletion of chain moieties at the natural N-terminus, as is demonstrated by the PTH fragment hPTh(28-48), results in a PTH fragment which will not stimulate renal adenylate cyclase; see Adv. Protein Chemistry, 35 (1982) 323 ff. (9; Potts et al.). Accordingly, it was not to be expected that, upon a deletion of amino acid residues from the chain structure of PTH, that the mitogenic action would not also be lost.

SUMMARY OF THE INVENTION

The invention is to provide pPTH, bPTH or hPTH modifications, and therapeutic compositions with those modifications, that do not stimulate renal adenylate cyclase but, rather, effect only chondrocyte proliferation; that is to say, they exhibit a mitogenic and bone-specific effect.

The terms "pPTH", "bPTH" and "hPTH" as used throughout the specification and claims have their normally accepted meaning, i.e.; parathyroid hormone with the source indicated by "p" (porcine), "b" (bovine) or "h" (human).

Modified PTH is available commercially or can be obtained from PTH by conventional and known peptide degradation methods.

Figure 10:
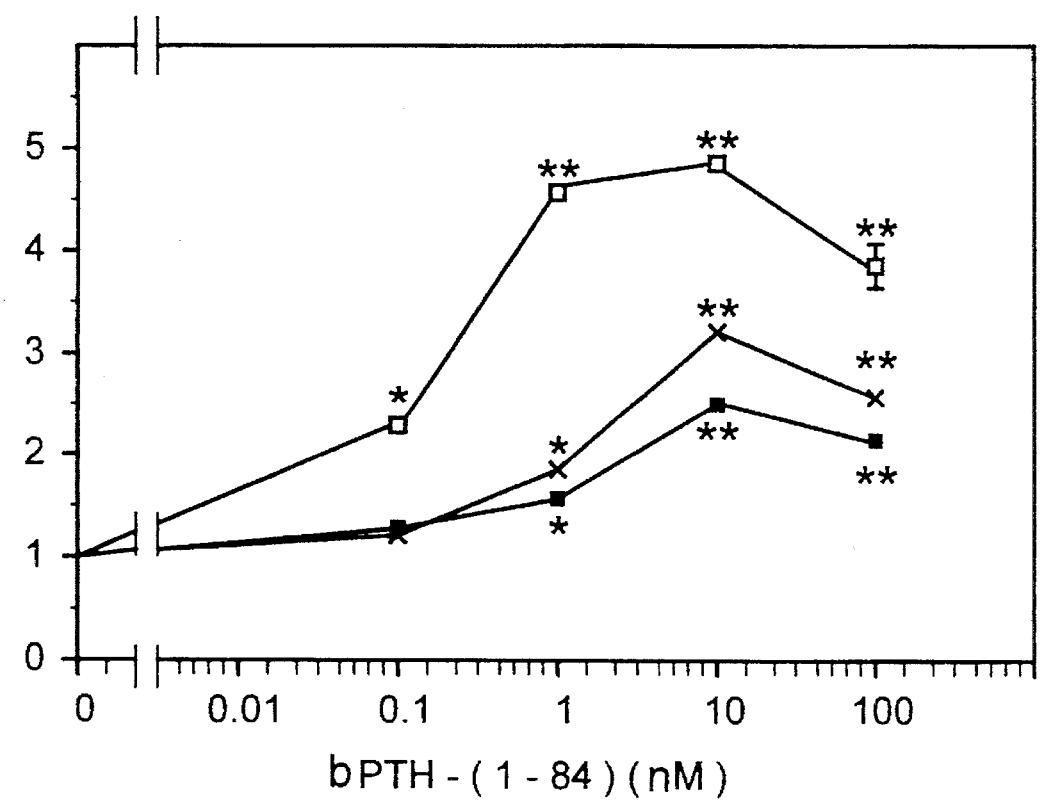
FIG. 10 is a graphical representation showing the dose dependent stimulation by bPTH (1-84) of osteoblast enriched rat embryo calvaria cell cultures. Experimental details for the determination of cyclic AMP (□) (15 min after stimulation) and incorporation of [$^3$H]thymidine into DNA (▲) and CK (● specific activity (24 h after stimulation) are given below. The results are means ±S.E.M., N≧5. In several cases the S.E.M. was less than the size of the symbol. Control values were: cyclic AMP, 25±5 pmol/mg of protein; DNA, 240±30 c.p.m./µg of DNA; CK, 200±20 nmol/min per mg of protein. Statistical significance of differences between treated and corresponding control groups by Student's T test: *P<0.05; **P<0.01.
Figure 11:
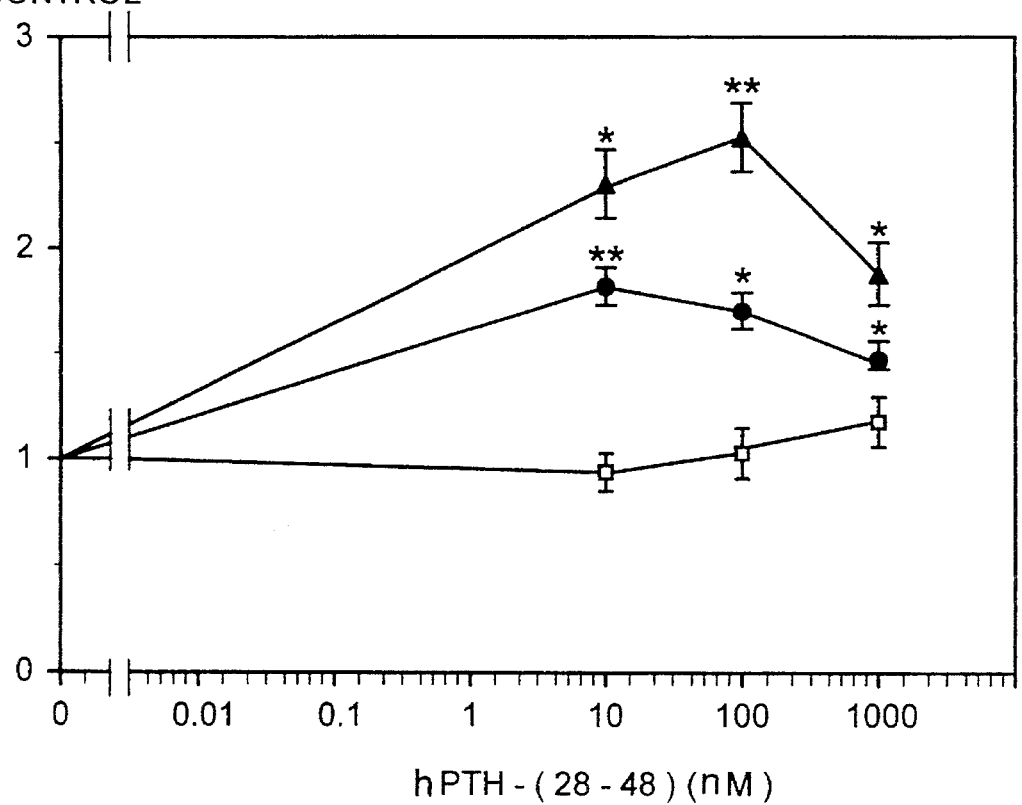
FIG. 11 is a graphical representation of the dose dependent stimulation by hPTH (28-48) of osteoblast enriched rat embryo calvaria cell cultures. Experimental details and symbols are the same as for FIG. 10. Control values are: cyclic AMP, 32±5 pmol/mg of protein; DNA, 630±30 c.p.m./µg of DNA; CK, 225±50 nmol/min per mg of protein.

Female rats (20–25 days old) were injected i.p. with hPTH-(1-34). At 4 h later, rats were killed and extracts were prepared and assayed as described below. Experimental details are as described for FIG. 10 (a) Diaphysis, (b) epiphysis, (c) kidney. *P<0.05, ** P<0.01 versus controls.

Figure 15A:
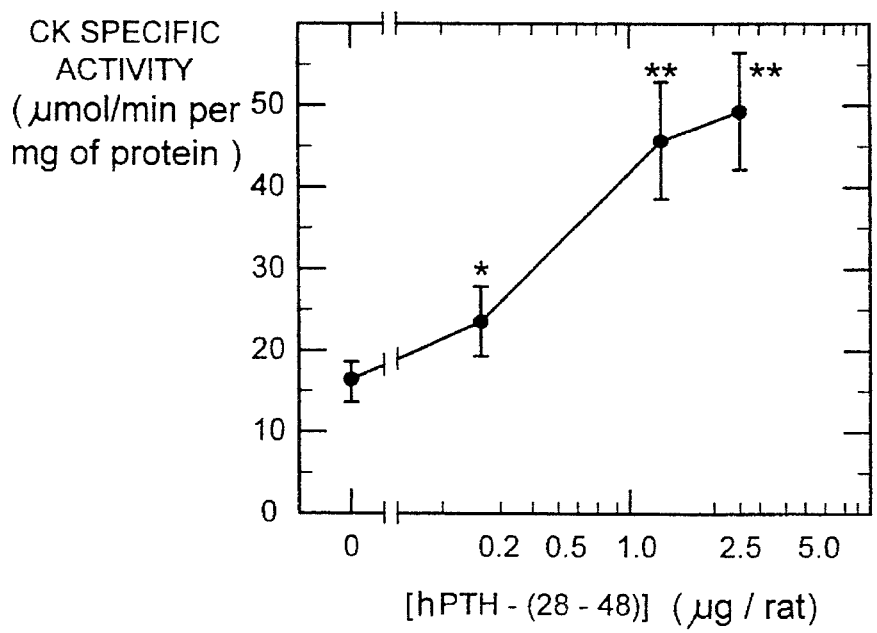
Figure 15B:
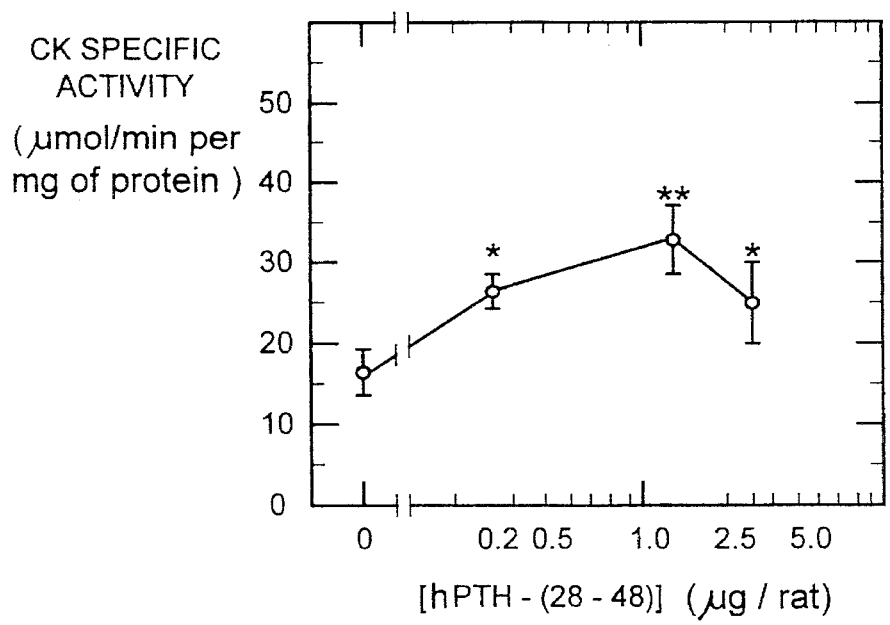
Figure 15C:
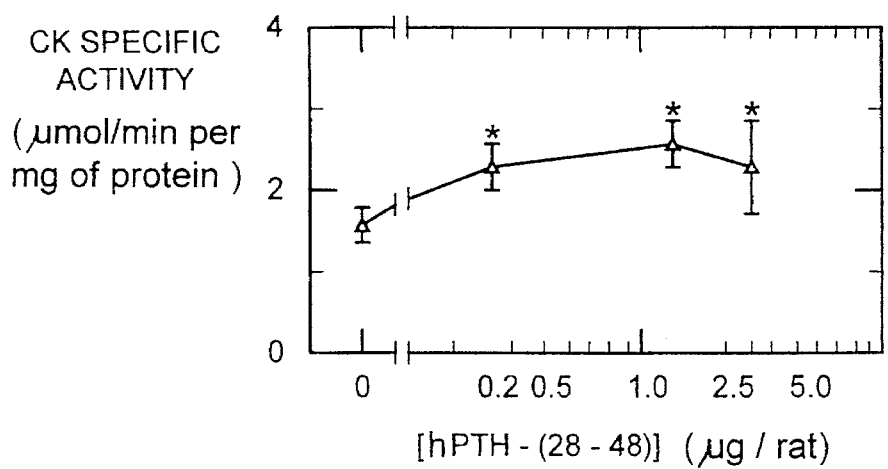

FIG. 15 is a graph showing the dose-dependent stimulation of CK specific activity by hPTH (28-48) in rat organs. Female rats (20–25 days old) were injected i.p. with hPTH-(28-48). Experimental details are as described for FIG. 13 (a) Diaphysis, (b) epiphysis, (c) kidney. *P<0.05, **P<0.01 versus controls.

Figure 16A:
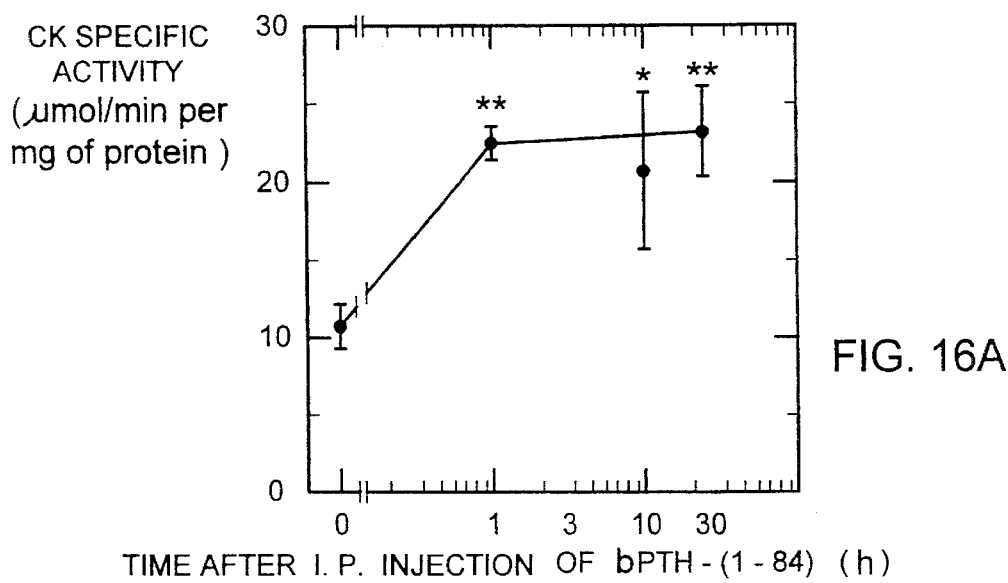
Figure 16B:
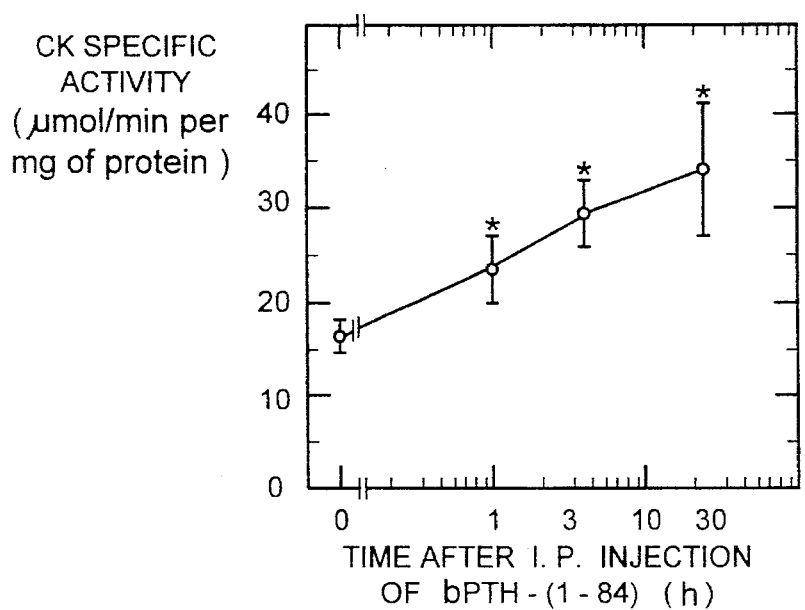
Figure 16C:
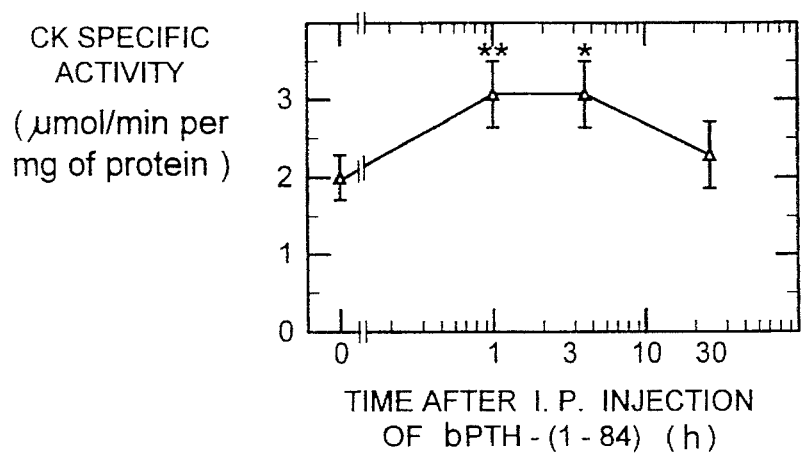

FIG. 16 is a graph showing the dose-dependent stimulation by bPTH (1-84) of CK specific activity in rat organs. Female rats (20–25 days old) were injected i.p. with bPTH-(1-84) (3.5 μg/rat). At the times indicated, the rats were killed and the diaphyses (a) and epiphyses (b) of long bones as well as the kidneys (c) were collected and homogenized. Extracts were prepared and assayed as described below. Results are means ±S.E.M for $n=5$. Statistical significance of differences between treated and control groups by Student's T test: *P<0.05; **P<0.01. Note that the activity scales differ for different organs.

DETAILED DESCRIPTION OF THE PREFERRED EMBODIMENTS OF THE INVENTION

The following examples, when read in conjunction with a viewing of the accompanying drawings of FIGS. 1–16, inclusive, describe the manner and process of making and using the invention and set forth the best mode contemplated by the inventors for carrying out the invention.

EXAMPLES 1 TO 3 AND COMPARATIVE EXAMPLE 1

The mitogenic effect was demonstrated by means of:

bPTH (1-84) (comparative example 1)

bPTH (1-34) (example 1)

bPTH (3-34) (example 2)

hPTH (28-48) (example 3)

Figure 1:
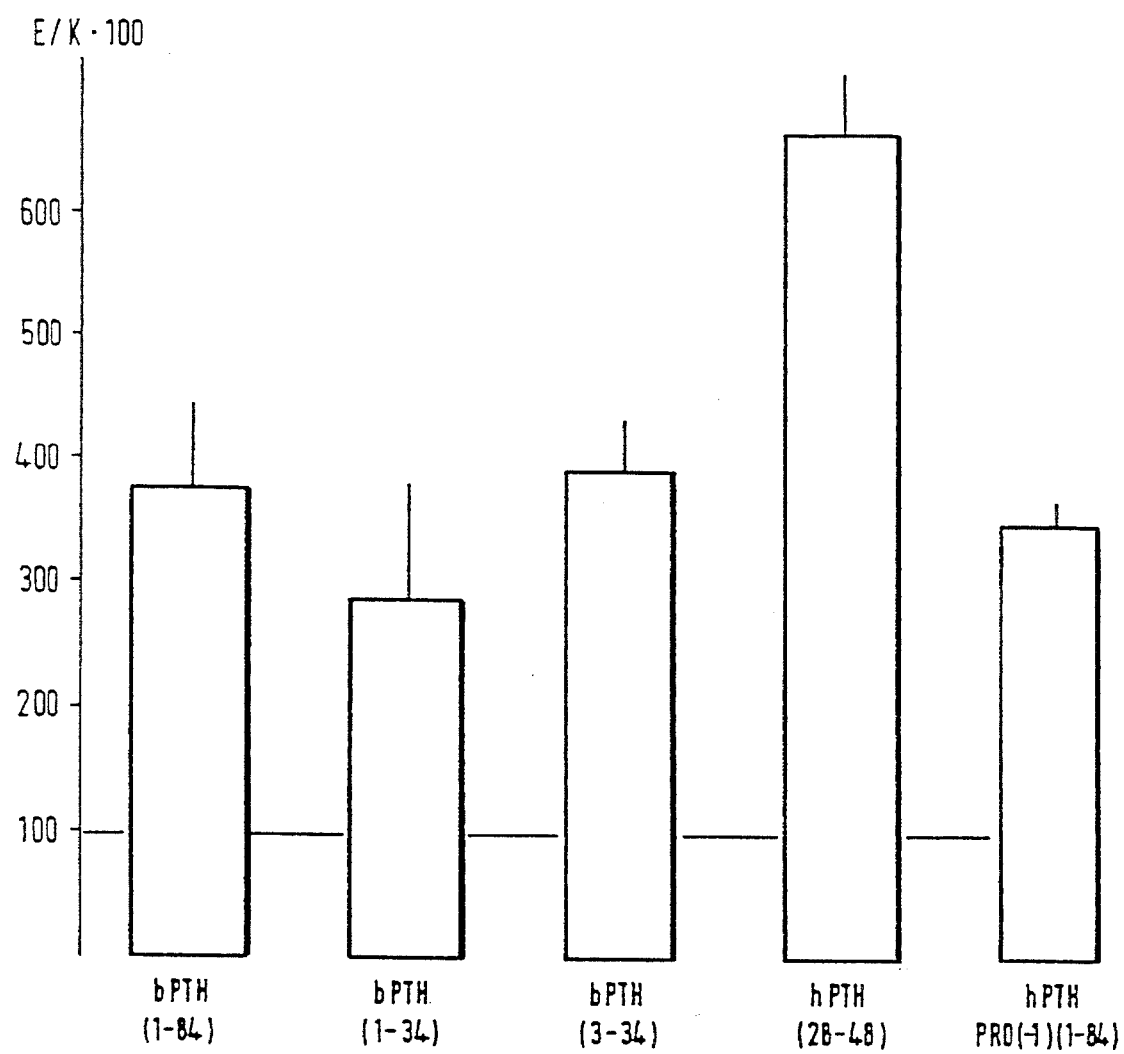
FIG. 1 is a graph showing the stimulation of chondrocyte DNA synthesis by the addition of PTH and PTH fragments; expressed as the ratio of the rate of incorporation of $^3$H-methylthymidine into the total DNA of the induced cultures to that of the untreated control cultures.
Figure 3:
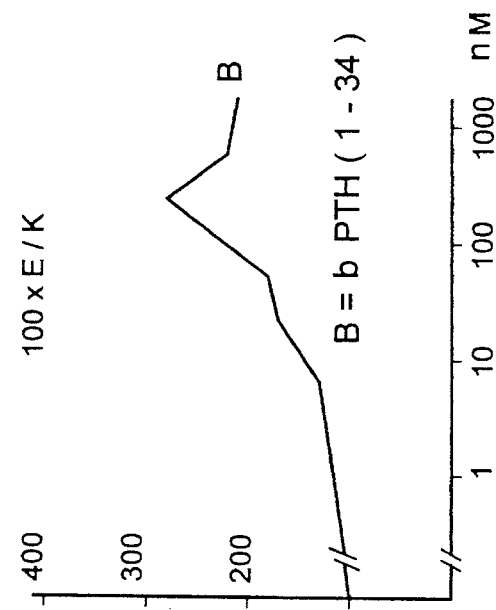
FIGS. 2–6 are graphs showing the dosage/effect curves for the mitogenic activity of PTH and PTH fragments.
Figure 2:
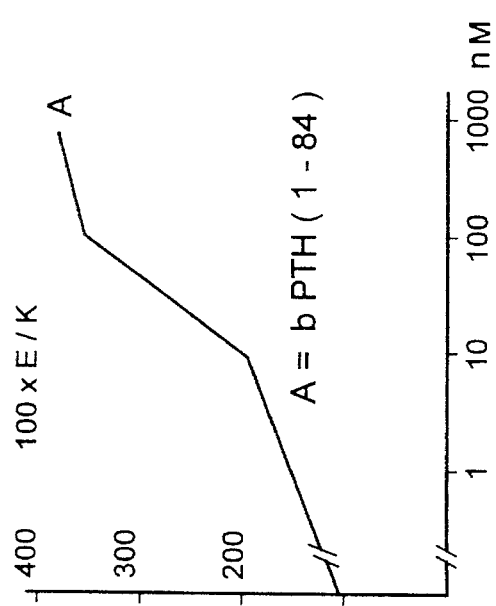
Figure 4:
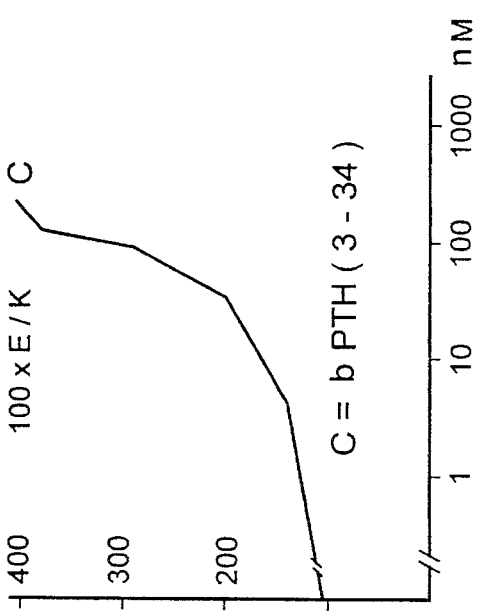
Figure 6:
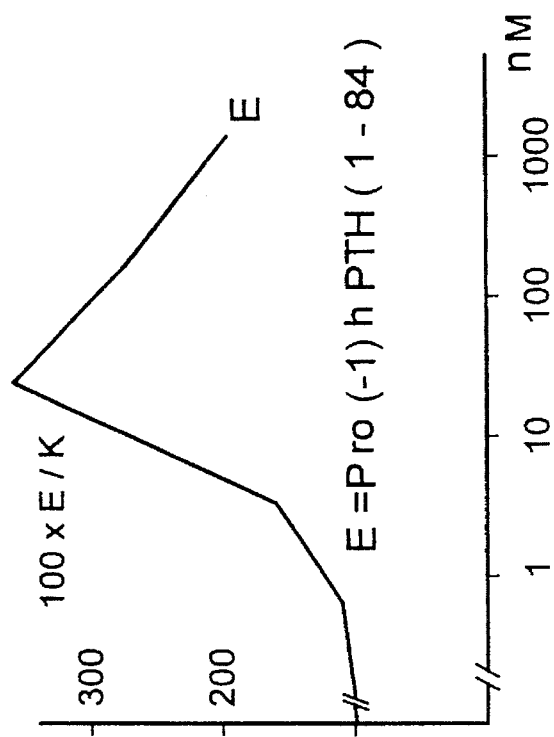
Figure 5:
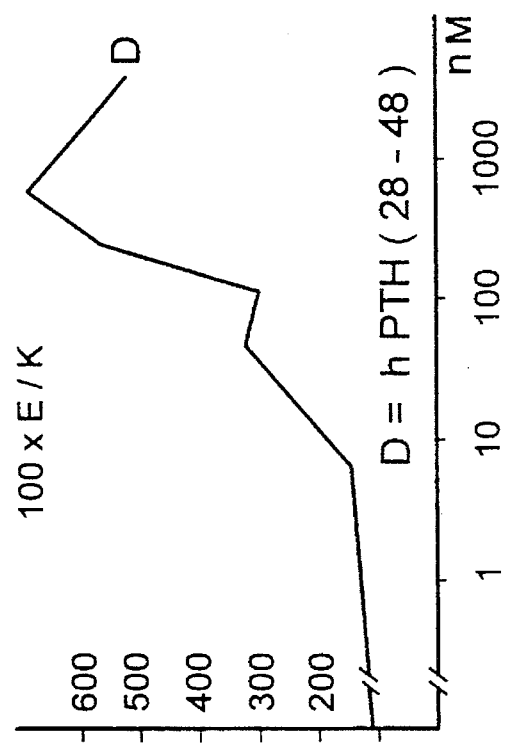
Figure 7:
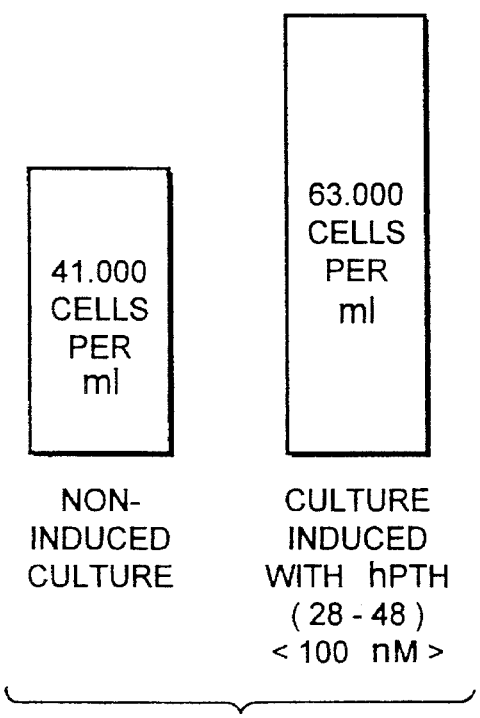
FIG. 7 is a comparative graph showing cell number after incubation of the non-induced cultures compared to cultures induced with hPTH (28-48) for 24 hours.
Figure 8:
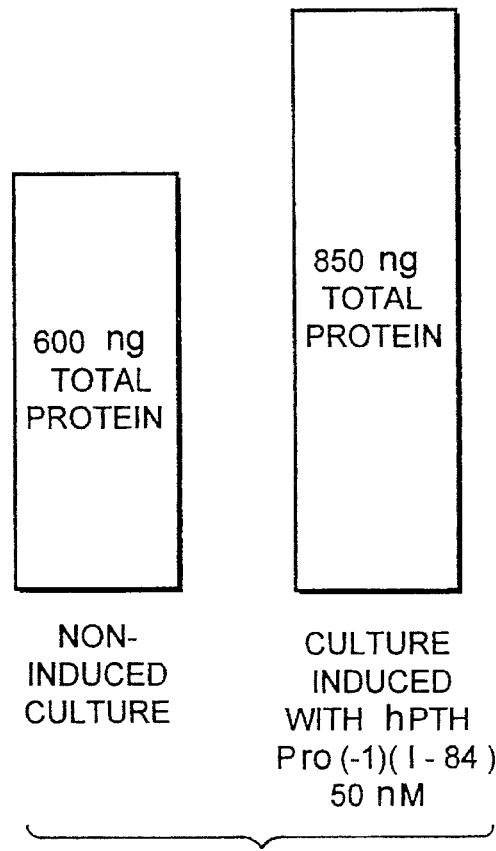
FIG. 8 is a comparative graph showing protein content after incubation of non-induced cultures compared to cultures induced with hPTH Pro(-1)(1-84) for 48 hours.
Figure 9:
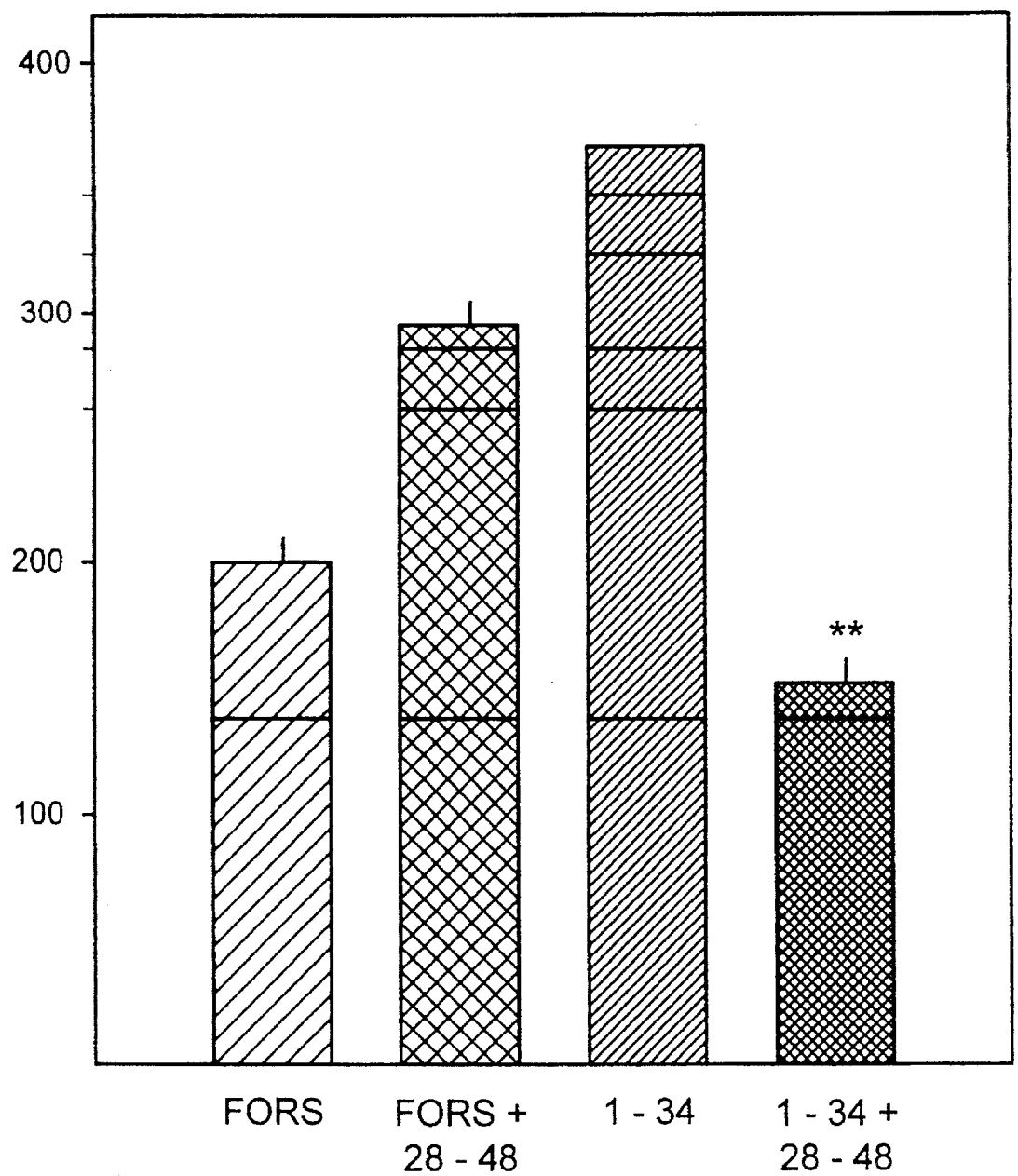
FIG. 9 is a graphical representation showing the cAMP yields [nitrogenic effect of bPTH (1-34).

The action according to the invention was demonstrated on chondrocytes that had been isolated by fractional collagenase treatment from the sterna of 16-day-old chicken embryos in accordance with the method described in J. Biol. Chem., 261 (1986) 7997–8001 (10; Yasui et al.). The growth-stimulating effect was demonstrated by the incorporation of $^3$H-methyl-thymidine into total DNA (FIG. 1), determination of cell number (FIG. 7) and determination of the total protein content of the cultures (FIG. 8). FIG. 1: In order to determine the incorporation of $^3$H-methylthymidine into total DNA the cells were cultivated on microtiter plates in M199 medium at a concentration of foetal calf serum (FCS) of less than 0.5% (by volume). The cell density of the chondrocytes that reacted to the addition of PTH with an increase in the incorporation of $^3$H-methylthymidine into the total DNA was from 1250 to 6000 cells/microtitre well (diameter 6 mm) at the time of plating-out. A maximum response was achieved at a cell density of 3000 cells/microtitre well (diameter 6 mm) at the time of plating-out within 4 to 12 hours of the addition of PTH and after growth of the chondrocytes, without changing the medium, for from 4 to 10 days. The incorporation of $^3$H-methylthymidine into the total DNA was determined as follows. After removing the radioactive medium, the adherent growing chondrocytes were washed with PBS and lysed in the microtitre wells. The total DNA was then precipitated under acid conditions at low temperature and transferred onto filter papers using a semi-automatic harvesting device. The rate of incorporation into total DNA could then be determined; cf. FIG. 1. FIG. 2: bPTH(1-84), FIG. 3: bPTH(1-34) and FIG. 4: bPTH(3-34) show a significant increase in the incorporation of $^3$H-methylthymidine into total DNA by a factor in the range of from 3.0 to 3.5 depending on the concentration of the PTH or PTH fragment added (FIG. 2). The concentration for semi-maximum stimulation was from 9 to 15 nM for bPTH(1-84) and from 50 to 75 nM for the PTH fragments bPTH(1-34) and bPTH(3-34). In contrast, the PTH fragment hPTH(28-48), which, according to Adv. Protein Chemistry, 35 (1982) 323 ff. (9; Potts et al.), does not stimulate renal adenylate cyclase and does not bind to the renal PTH receptor, showed an increased incorporation by a factor of 6 at a concentration for semi-maximum stimulation of 349 nM. FIG. 7: hPTH(28-48) further resulted in an increase in the total cell number from 41,000 cells/ml to 63,000 cells/ml.

EXAMPLE 4

In this example the mitogenic effect was demonstrated by means of hPTH(28-48).

100 nM bPTH(1-34) were used to stimulate cAMP synthesis of intact ROS 17/2.8 cells (cell density $1.3 \times 10^6$ cells/cm$^2$) in the presence of 1 mM IBMX for 10 min. cAMP yields were determined by radio assay. Based on the conditions mentioned, the cAMP basal value of non-stimulated cells corresponds to 8 pmol/well. This effect of bPTH(1-34) can be inhibited by an additional doses of 30 nM hPTH(28-48) up to about 50%; cf. FIG. 9.

This result is unexpected in view of the fact that an increase of cAMP synthesis is an essential step of the bone degrading effect of PTH. In other words, hPTH(28-48) as an example for a mid-regional PTH fragment can, in addition to its direct anabolic effect, suppress catabolic hormonal effects of N-terminally intact PTH, such as PTH(1-34) and PTH(1-84), simultaneously present.

EXAMPLES 6 TO 22 AND COMPARATIVE EXAMPLES 2 TO 11

Chondrocytes were isolated from sterna of 16-day-old embryonic chicks according to J. Biol. Chem., 261 (1986) 7997–8001 (10; Yasui et al.) with some modifications. Collagenase was dissolved in Hanks' balanced salt solution (0.4 mM Na$_2$HPO$_4$, 140 mN NaCl, 5.3 mM KCl, 0.4 mM MgSO$_4$, 1.3 mM CaCl$_2$, 0.4 mM KH$_2$PO$_4$, 0.5 mM MgIC$_2$, 5 mM glucose, 0.05% gentamicin) at a concentration of 286 units/ml. Sterna were treated repeatedly for 30 min with collagenase solution at 37° C. Cells first released by this procedure were discarded because of their very poor responsiveness towards PTH. The collagenase treatment was subsequently repeated leading to a highly homogenous cell population of chondrocytes. The cells obtained by a second collagenase treatment were collected by centrifugation (1000 rpm, 10 min), washed twice with medium (Dulbecco's modified Eagle's medium, GIBCO, supplemented with NaHCO$_3$ (45 mM), glutamine (2 mM), penicillin G/streptomycin (65 mg/l and 100 mg/l, respectively), Hepes (10 mM, pH 7.2), and FCS (10% v/v) and counted.

The DNA synthesis rate was assayed in monolayer culture by the incorporation of ]$^3$H]thymidine into perchloric acid-precipitable material. After variation of the essential parameters, the following conditions were found to be optimal to assay the stimulation of thymidine incorporation by PTH: cells were seeded into microtiter plates with 96 wells (6-mm diameter; 14,000 cells/cm$^2$) and a 200-μl volume of medium containing 10% FCS and were incubated at 37° C. in an atmosphere of 5% $CO_2$. After 17 h, the medium was replaced by 200 μl of serum-free medium. After 4 days, chondrocytes were incubated for 4 h with the appropriate effector and 1μ Ci of [$^3$H]thymidine. Subsequently, medium was removed and the cells were washed twice with 200 μl of phosphate-buffered saline (PBS: 137 mM NaCl, 2.7 mN KCl, 1.5 mM $KH_2PO_4$, 0.8 mN $Na_2HPO_4$, pH 7.0). Then cells were lysed by 100 μl of 2% (v/v) Nonidet P- 40 and 2% (w/v) sodium dodecyl sulfate treatment and the perchloric acid-insoluble material was precipitated by adding an equal volume of ice-cold 2% (w/v) perchloric acid in the presence of 1% herring sperm DNA as carrier. After storage for 10 min at −20° C., the precipitated material of each well was transferred to glass fiber filters with a Scatron—As semiautomatic cell harvester. Filters were dried at 80° C. for 20 min, transferred into scintillation vials, and 2 ml of scintillation mixture (scintillator 299; United Technology Pachard) were added. Radioactivity of the samples was determined with a β counter (Minimax; United Technology Pachard). Each test consisted of 5 up to 10 identically treated wells and was repeated at least twice with freshly prepared chondrocytes.

The results obtained can be taken from the following table. The incorporation of [$^3$H]thymidine by non-induced control cells and by stimulated cells is shown by C and E, respectively. The results shown mean ±S.E. for n parallel cell cultures.

EXAMPLES 23 TO 25 AND COMPARATIVE EXAMPLES 12 TO 15

MITOGENIC ACTIVITY OF PTH FRAGMENTS ON RAT OSTEOBLAST-ENRICHED CALVARIA CELL CULTURES

Rat calvaria cultures were treated with fragments of PTH derived from the central portion of the molecule. When treated for 15 min for stimulation of cyclic AMP production (Table 2), only the complete PTH containing the N-terminal part of the molecule or hPTH(1-34); results not shown] was able to stimulate cyclic AMP formation; all other peptides tested were ineffective. When cells were treated for 24 h and CK activity was measured (Table 2), bPTH(1-84) [as well as (hPTH(1-34); results not shown], hPTH(29-39), hPTH(28-48) and hPTH(32-47) were maximally active in increasing CK activity, whereas hPTH(29-47) was stimulatory but to a lesser degree, and hPTH(30-47) was slightly stimulatory. All other fragments used [hPTH(31-47), hPTH(33-47), hPTH(33-47) and hPTH(34-47)] were inactive.

When DNA synthesis was measured, the stimulation by the different fragments was found to be maximal with bPTH(1-84) [as well as with hPTH(1-34); results not shown], hPTH(25-39) and hPTH(28-48), and less with hPTH(28-47) (Table 2).

EXAMPLES 26 TO 27 AND COMPARATIVE EXAMPLES 16 TO 18

MITOGENIC ACTIVITY OF PTH FRAGMENTS ON RAT EPIPHYSEAL CARTILAGE CELL CULTURES

To compare the stimulations seen in osteoblast-like cells (FIGS. 10 and 11) with PTH effects in a cartilage system, cultures of rat epiphysial cartilage cells were incubated with full-length PTH and selected PTH fragments (Table 3). CK activity was stimulated by bPTH(1-84) and hPTH(28-48) but not by hPTH(25-39) or hPTH(34-47). However, DNA synthesis was stimulated by all molecules tested except hPTH(34-47) (Table 3). The comparison between the complete molecule and the mid-regional fragment hPTH (28-48) is similar to but not identical with the results obtained for calvaria cell cultures (FIGS. 10 and 11) and in the chick sternum chondrocyte system; cf. Biochem. J., 252 (1988) 263–268 (11; Farndale et al.),

EXAMPLES 28 TO 31 AND COMPARATIVE EXAMPLES 19 TO 20

MITOGENIC ACTIVITY OF PTH FRAGMENTS ON ROS 17/2.8 OSTEOSARCOMA CELL CULTURES

When cultures of the widely used model for osteoblasts, the osteoblast-like clone of rat osteosarcoma, ROS 17/2.8 (Endocrinology (Baltimore), 107 (1980) 1494–1503=12; Majeska et al.), were incubated with full-length PTH and PTH fragments (Table 4), cyclic AMP production was stimulated only by bPTH(1-84) and hPTH(1-34), whereas hPTH(25-39), hPTH(27-48), hPTH(28-48) and hPTH(34-47) were ineffective. Both CK activity and DNA synthesis were stimulated by all of the cell fragments tested except hPTH(24-47) (Table 4). These results are also similar to the results obtained in calvaria cell cultures.

EXAMLPES 32 TO 35 AND COMPARATIVE EXAMPLES 21 TO 26 CK ASSAY

Kidneys, tibia and femur were excised; the epiphyses or diaphyses of the long bones were collected and washed thoroughly with cold 0.9% NaCl. The bones were split open lengthwise and the marrow was scraped out. Organs were homogenized in ice-cold buffer containing 50 mM-Tris/HCl (pH 6.8), 5 mH-magnesium acetate. 2.5 mM-dithiothreitol, 0.4 mM-EDTA and 250 mM-sucrose using a Polytron homogenizer in 10 s bursts with intervening cooling periods. Supernatant extracts were obtained by centrifugation at 12000 g for 5 min at 4° C. CK activity was measured at 30° C. in a Gilford 250 automatic recording spectrophotometer at 340 nm using a coupled assay for ATP, in 0.5 ml of incubation mixture containing 50 mM-imidazole acetate buffer (pH 6.7), 25 mM-phosphocreatine, 20 mM-N-acetyl-cysteine, 20 mM-D-glucose, 10 mM-magnesium acetate, 5 mM-EDTA, 2 mM-ADP, 2 mM-NAD+, 2 mM-dithiothreitol, 50 μM-diadenosine pentaphosphate (adenylate kinase inhibitor), 5 μg of bovine serum albumin. 1.2 units of glucose-6-phosphate dehydrogenase and 0.8 units of hexokinase. Protein was determined by the Coomassie Brilliant Blue dye-binding method, with bovine serum albumin as the standard.

[$^3$H]THYMIDINE INCORPORATION INTO DNA

At 0.2, 14 and 22 h after injection, the rats were killed and the tissues were removed rapidly, washed and cut into cubes, approx. 2 mm per side which were found to give optimal incorporation. The pieces were then incubated for 2 h more (the time indicated in FIG. 12) with [$^3$H]thymidine (5 μci/ml; 5 Ci/mmol) at 37° C. in Dulbecco's modified Eagle's medium under an atmosphere Of 6% $CO_2$/95% air. Total [$^3$H]thymidine uptake and incorporation into trichloroacetic acid-insoluble material was measured as described in Biochem. J., 214 (1983) 293–298 (16; Somjen et al.). At no time including the 22 24 h pulse, was there any significant change in the total uptake of [$^3$H]thymidine which reflects changes in the thymidine pool which, in turn, could account for changes in incorporation. DNA was determined by the Burton method; cf. Biochem. J., 62 (1956) 315–323 (17; Burton).

Figure 13A:
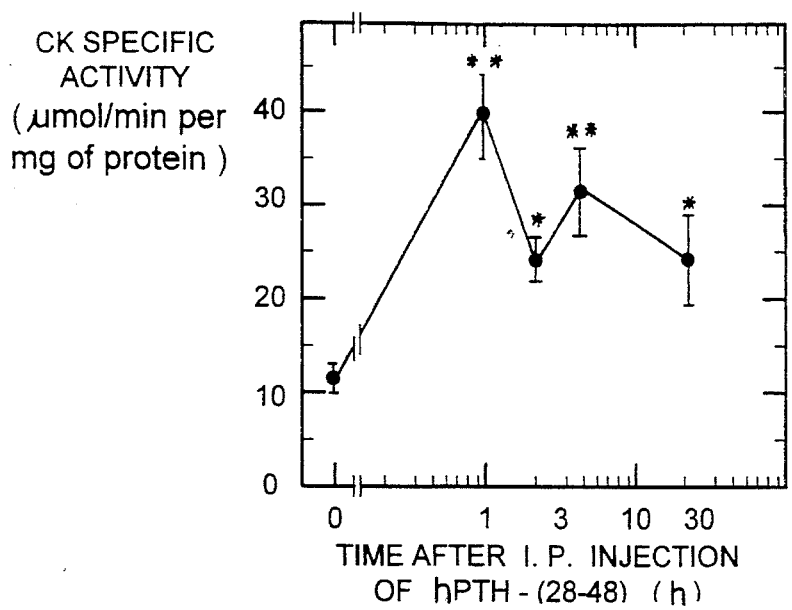
FIG. 13 is a graph showing the time-dependent stimulation by hPTH (28-48) of CK specific activity in rat organs. Female rats (20–25 days old) were injected i.p. with hPTH-(28-48) (1.25 µg/rat). Experimental details are as described for FIG. 10. (a) Diaphysis, (b) epiphysis, (c) kidney. *P<0.05, **P<0.01 versus controls.
Figure 13B:
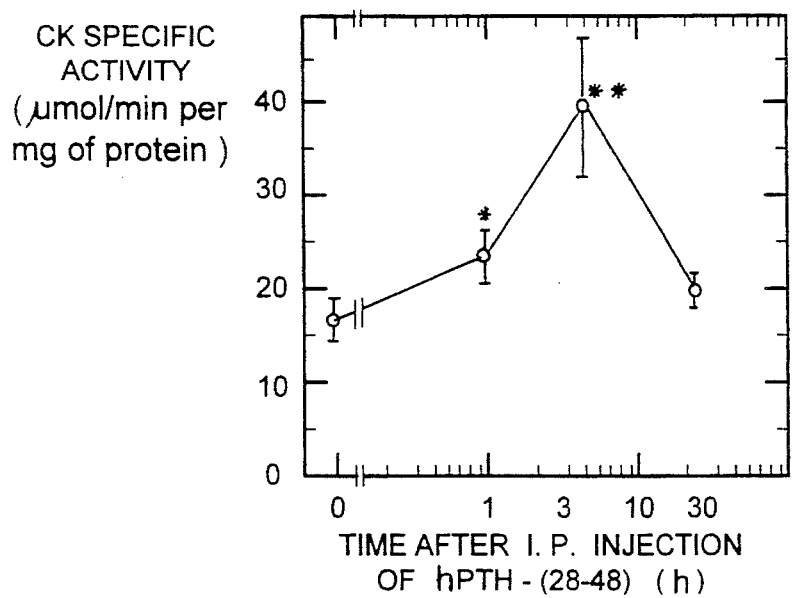
Figure 13C:
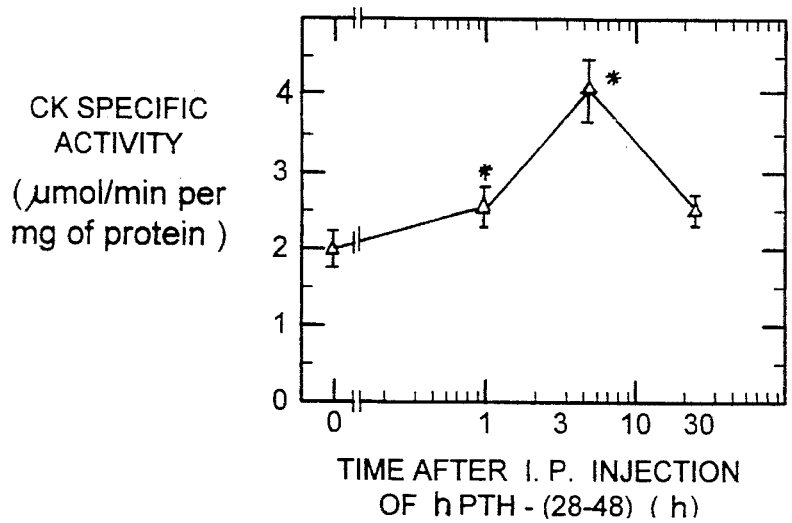
Figure 14A:
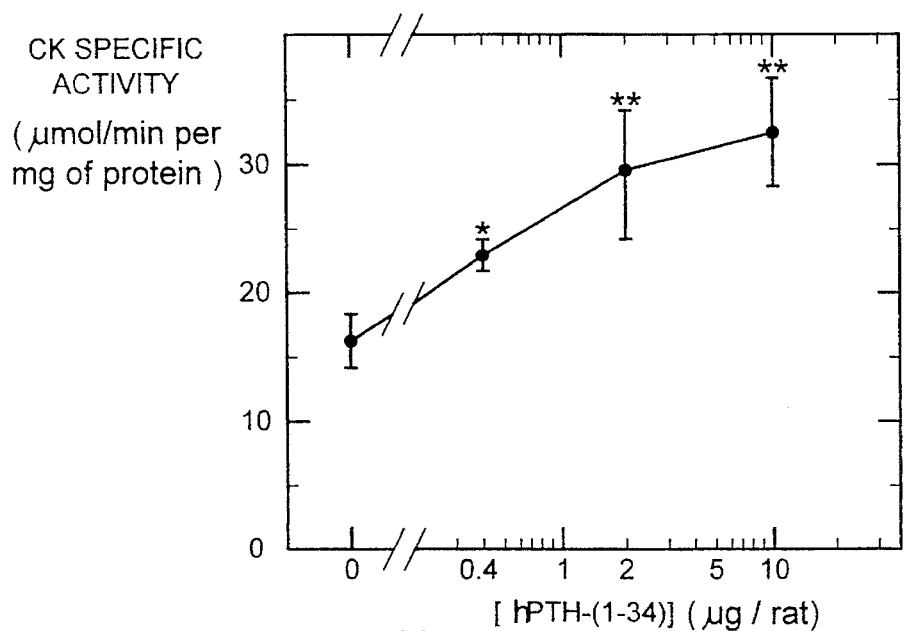
FIG. 14 is a graph showing the dose-dependent stimulation of CK specific activity by hPTH (1-34) in rat organs.
Figure 14B:
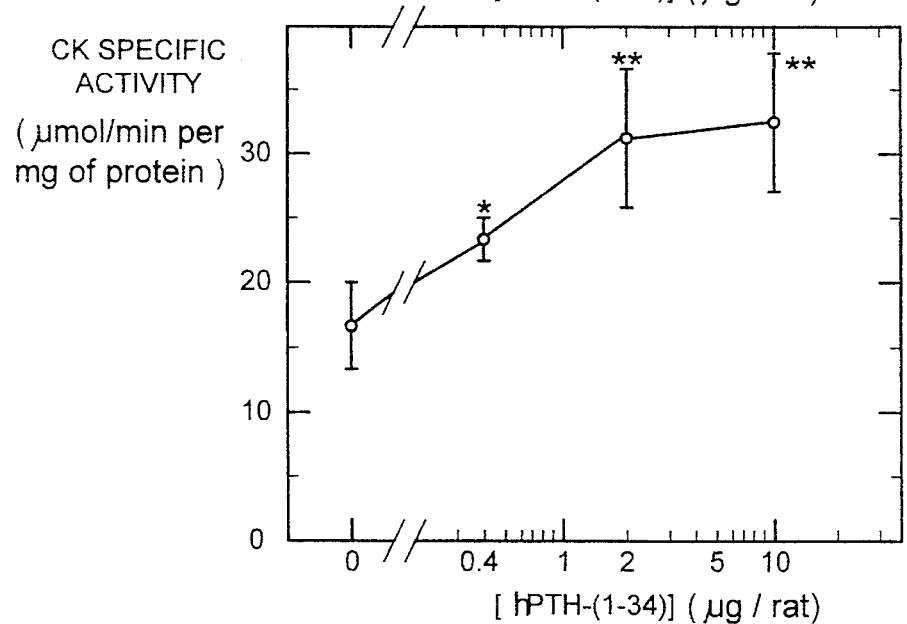
Figure 14C:
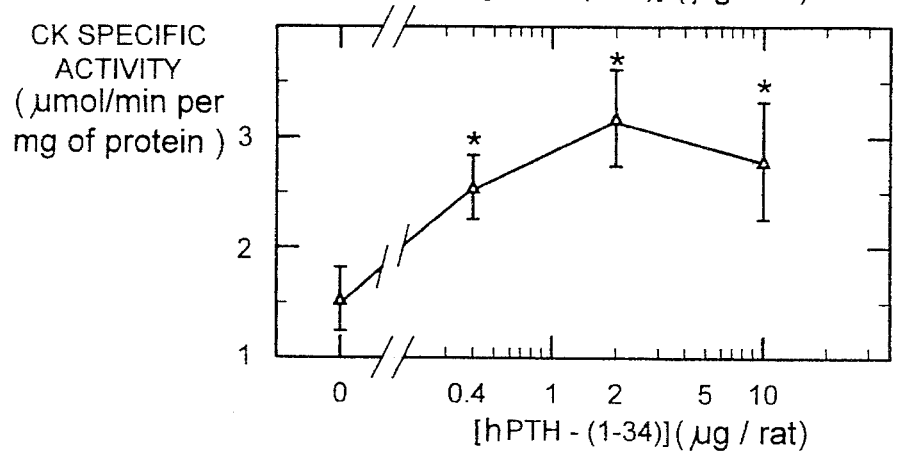

The mid-portion fragment hPTH(28-48). which has mitogenic activity in vitro, also increased CK activity after injection of 1.25 μg/rat, equivalent to 14 nM (FIG. 13). In kidney, CK specific activity increased to a peak between 1 and 4 h and then declined to close to the constitutive activity at 24 h. In the epiphysis there was a significant increase at 1 h, a maximal increase at 4 h and no significant increase at 24 h. However, in the diaphysis, CK activity was significantly increased at all three times measured, with the maximal increase at 1 h. Injection of rats with increasing doses of PTH(1'4 34) caused a significant increase in CK specific activity 4 h later in all organs at the lowest dose tested (0.4 μg/rat) to a maximal value at 2 μg/rat, equivalent to 13 nM (FIG. 14). When rats were injected with hPTH(28-48) and killed 4 h later, a similar result was obtained (FIG. 10); there was a significant increase in CK specific activity in all three organs at a dose of 0.15 μg/rat, with a maximum effect at 1.25 μg/rat (equivalent to 14 nM), which reached an approx. 3-fold stimulation in diaphysis.

COMPARISON OF EFFECTS OF DEFINED PTH FRAGMENTS ON CK ACTIVITY AND DNA SYNTHESIS IN RAT ORGANS

To compare the activity of PTH(28-48) (FIG. 15), with that of other fragments derived from the mid region of PTH, rats were injected with hPTH(25-39) or hPTH(34-47) at a dose of 0.875 μg/rat, equivalent to 14 nM; whereas hPTH(25-39) caused a significant increase in CK activity, hPTH(34-47) had no effect (Table 6).

Figure 12A:
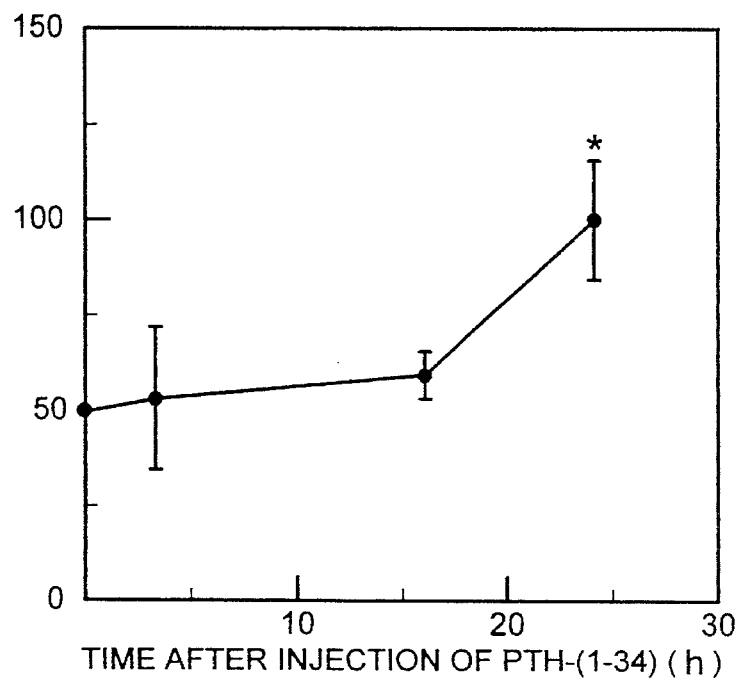
FIG. 12 is a graph showing the time course of stimulation by hPTH (1-34) of DNA synthesis in rat organs. Female rats (20–25 days old) were injected i.p. with hPTH-(1-34) (2 µg/rat). At 2 h before the times indicated, the rats were killed and organs were removed and incubated in 2 ml of Dulbecco's modified Eagle's medium containing 5 µl of [$^3$H] thymidine. (Amersham: 5 Ci/mmol) for 2 h, then washed with medium and homogenized in deionized distilled water. The total uptake of [$^3$H]thymidine and acid-insoluble radioactivity was measured, as well as DNA content, as described below. ●Diaphysis; O, epiphysis; ∆; kidney. P<0.01 versus controls.
Figure 12B:
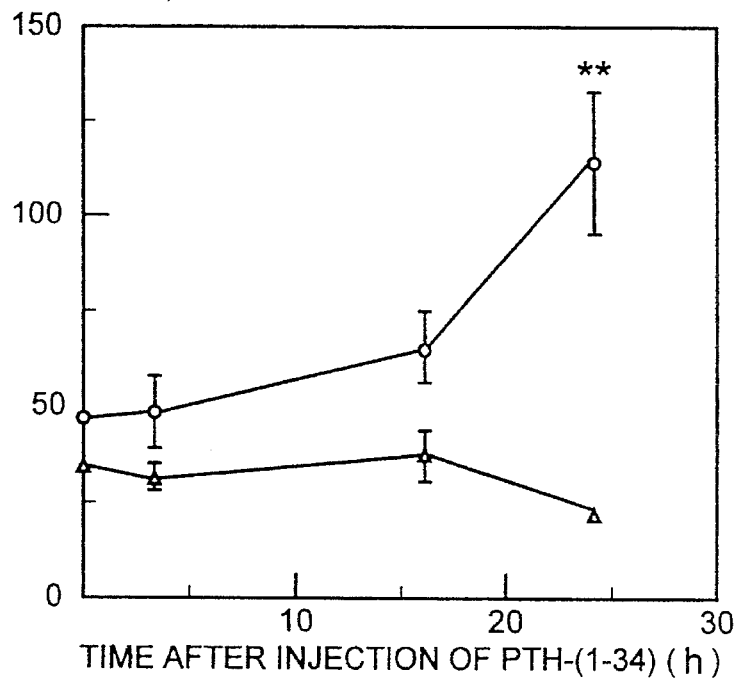

To corroborate that under the circumstances of these experiments the increase in CK specific activity in bone is indeed a valid marker of cell proliferation, changes in DNA synthesis were measured by [$^3$H]thymidine incorporation; cf. Biochem. J., 272 (1990) 781–785 (18; Sömjen et al.). The earliest time at which PTH increased [$^3$H]thymidine incorporation was determined by in-jecting rats with an optimal dose of 2 μp of PTH(1-34)/rat, equivalent to 13 nM (FIG. 14) and measuring 2 h pulses of [$^3$H)thymidine incorporation into DNA (FIG. 12). In the kidney, unlike the increase in CK activity, there was no increase in DNA synthesis at any time. In the diaphysis and the epiphysis there was no change at 4 or 16 h, but at 24 h there was a significant increase in DNA synthesis (FIG. 2). Therefore rats were injected with test compounds and 22–24 h later [$^3$H]thymidine incorporation into DNA was measured in vitro, hPTH(25-39) was as potent as hPTH(28-48) in stimulating [$^3$H]thymidine incorporation, which in turn was as potent as bPTH(1-84) in diaphysis and epiphysis, whereas hPTH(34-47) was inactive. In the kidney there was no significant stimulation of DNA synthesis by any of the fragments tested or by bPTH(1-84) (Table 6), since after the age of 16 days there is negligible cell division in rat kidney, which grows by hypertrophy.

TABLE 1

Stimulation of DNA synthesis in chondrocytes by PTH fragments

| Ex. | Comp. ex. | Stimulation agent | Concentration mol/l | Cultures (n) | [$^3$H]thymidine incorporation cpm | E/C |
|---|---|---|---|---|---|---|
|  | 2 | None |  | 30 | 139 ± 6 | (1.00) |
| 5 |  | hPTH(28-47) | 4.5 × 10$^{-8}$ | 10 | 196 ± 25 | 1.41[a] |
| 6 |  |  | 4.5 × 10$^{-7}$ | 10 | 205 ± 22 | 1.47[b] |
| 7 |  |  | 4.5 × 10$^{-6}$ | 10 | 202 ± 17 | 1.45[b] |
| 8 |  |  | 4.5 × 10$^{-5}$ | 10 | 276 ± 36 | 1.99[b] |
| 9 |  | hPTH(29-47) | 4.8 × 10$^{-8}$ | 10 | 138 ± 15 | 0.99[b] |
| 10 |  |  | 4.8 × 10$^{-7}$ | 10 | 273 ± 33 | 1.96[b] |
| 11 |  |  | 4.8 × 10$^{-6}$ | 10 | 225 ± 20 | 1.62[b] |
| 12 |  |  | 4.8 × 10$^{-5}$ | 10 | 273 ± 30 | 1.96[b] |
|  | 3 | hPTH(30-47) | 5.1 × 10$^{-8}$ | 10 | 169 ± 23 | 1.22 |
|  | 4 |  | 5.1 × 10$^{-7}$ | 10 | 222 ± 19 | 1.60[b] |
|  | 5 |  | 5.1 × 10$^{-6}$ | 10 | 193 ± 20 | 1.39[a] |
|  | 6 |  | 5.1 × 10$^{-5}$ | 10 | 248 ± 31 | 1.78[b] |
|  | 7 | hPTH(31-47) | 5.3 × 10$^{-8}$ | 10 | 165 ± 20 | 1.19 |
|  | 8 |  | 5.3 × 10$^{-7}$ | 10 | 178 ± 24 | 1.28 |
|  | 9 |  | 5.3 × 10$^{-6}$ | 10 | 178 ± 35 | 1.28 |
|  | 10 |  | 5.3 × 10$^{-5}$ | 10 | 176 ± 8 | 1.27[a] |
|  | 11 | None |  | 10 | 324 ± 18 | (1.00) |
| 13 |  | hPTH(25-39) | 6.1 × 10$^{-8}$ | 5 | 452 ± 56 | 1.40[c] |
| 14 |  |  | 6.1 × 10$^{-7}$ | 5 | 418 ± 41 | 1.29[c] |
| 15 |  |  | 6.1 × 10$^{-6}$ | 5 | 517 ± 65 | 1.60[a] |
| 16 |  |  | 6.1 × 10$^{-5}$ | 5 | 655 ± 147 | 2.02[a] |
| 17 |  |  | 6.1 × 10$^{-4}$ | 5 | 542 ± 71 | 1.67[a] |
| 18 |  | hPTH(28-39) | 7.6 × 10$^{-8}$ | 5 | 319 ± 39 | 0.97 |
| 19 |  |  | 7.6 × 10$^{-7}$ | 5 | 473 ± 74 | 1.46 |
| 20 |  |  | 7.6 × 10$^{-6}$ | 5 | 324 ± 45 | 1.00 |
| 23 |  |  | 7.6 × 10$^{-5}$ | 5 | 399 ± 47 | 1.23 |
| 22 |  |  | 7.6 × 10$^{-4}$ | 5 | 387 ± 41 | 1.19 |

TABLE 1-continued

Stimulation of DNA synthesis in chondrocytes by PTH fragments

| Ex. | Comp. ex. | Stimulation agent | Concentration mol/l | Cultures (n) | [³H]thymidine cpm | incorporation | E/C |
|---|---|---|---|---|---|---|---|

[a] $p < 0.01$.
[b] $p < 0.001$.
[c] $p < 0.02$.

TABLE 2

Stimulation of cyclic AMP production. CK activity and DNA synthesis in rat embryo calvaria cell cultures by defined PTH fragments.
The results are means ± S.E.M.: n = 5–15 for at least two sets of cultures. Control values were: cyclic AMP, 29 ± 2.9 pmol/mg of protein; DNA, 624 ± 73 c.p.m./µg of DNA; CK 457 ± 46 nmol/min per mg of Protein. Statistical significance of differences between treated and control groups by Student's t test: *P < 0,05; **p < 0.01.

| | | | Effect of fragment (experimental value/control value) | | |
|---|---|---|---|---|---|
| Ex. | Comp. ex. | PTH fragment (100 nM) | Cyclic AMP concentration | CK specific activity | [3H]Thymidine incorporation |
| | 12 | None | 1.00 ± 0.10 | 1.00 ± 0.15 | 1.00 ± 0.11 |
| | 13 | bPTH(1-84) | 3.74 ± 0.30** | 2.27 ± 0.09** | 2.61 ± 0.11** |
| 23 | | hPTH(25-39) | 0.87 ± 0.30 | 2.15 ± 0.24* | 2.96 ± 0.18** |
| 24 | | hPTH(28-48) | 1.22 ± 0.09 | 2.15 ± 0.15** | 2.82 ± 0.18** |
| 25 | | hPTH(28-47) | 0.52 ± 0.39 | 2.18 ± 0.12* | 2.11 ± 0.09** |
| | 14 | hPTH(29-47) | 0.57 ± 0.47 | 1.67 ± 0.13* | 1.96 ± 0.14** |
| | 15 | hPTH(30-47) | 1.00 ± 0.22 | 1.27 ± 0.03* | 1.86 ± 0.18** |

TABLE 3

Stimulation of CK specific activity and DNA synthesis in rat epiphysial cartilage cell cultures by defined fragments of PTH
No significant increase in the amount of DNA per plate was detectable by 24 h.
The results are means ± S.E.M.; n = 6 for two sets of cultures. Statistical significance of differences between test and control groups by Student's t test: *P < 0.05; **P < 0.01.

| Ex. | Comp. ex. | PTH fragment | CK specific activity (nmol/min per mg of protein) | [³H]Thymidine incorporation into DNA (c.p.m./plate) |
|---|---|---|---|---|
| | 16 | Control | 225 ± 32 | 350 ± 25 |
| | 17 | bPTH(1-84) (10 nM) | 389 ± 39* | 556 ± 50* |
| 26 | | hPTH(25-39) (100 nM) | 268 ± 36 | 544 ± 44* |
| 27 | | hPTH(28-48) (100 nM) | 346 ± 36* | 731 ± 44** |
| | 18 | hPTH(34-47) (100 nM) | 236 ± 32 | 356 ± 75 |

TABLE 4 stimulation of cyclic AKP production, CK specific activity and DNA synthesis in ROS 17/2.8 osteoblast-like cells by defined PTH fragments
Concentrations were chosen on the basis of results obtained with chick sternum chondroblasts; cf. J. Biol. Chem,, 264 (1989) 11087–11092 (13; Schluter et al.). The results are means ± S.E.M. n >= 5. Control values were; cyclic AMP 29 ± 5.2 pmol/ mg of protein; DNA 392 ± 58 c.p.m./µg of DNA; CK 698 ± 70 nmol/min per mg of protein. Statistical significance of differences between treated and control groups of student's t test; 'P < 0.05; ,p < 0.01; *,p < 0.005.

| Ex. | Comp. ex. | PTH fragment | Effect of fragment (experimental value/control value) | | |
|---|---|---|---|---|---|
| | | | Cyclic AMP | CK specific activity | [$^3$H]Thymidine incorporation |
| | 19 | bPTH(1-84) (10 nM) | 4.60 ± 0.10*** | 1.92 ± 0.11** | 1.71 ± 0.18* |
| 28 | | hPTH(1-34) (40 nM) | 4.67 ± 0.09*** | 1.83 ± 0.09** | 2.06 ± 0.09** |
| 29 | | hPTH(25-39) (200 nM) | 1.05 ± 0.15 | 1.71 ± 0.08* | 1.36 ± 0.08* |
| 30 | | hPTH(28-47) (400 nM) | 1.03 ± 0.16 | 1.66 ± 0.11* | 1.44 ± 0.11* |
| 31 | | hPTH(28-48) (400 nM) | 1.18 ± 0.28 | 1.56 ± 0.08* | 1.56 ± 0.12* |
| | 20 | hPTH(34-47) (500 nM) | 0.88 ± 0.31 | 1.07 ± 0.10 | 1.05 ± 0.11 |

TABLE 5

Stimulation of CR specific activity by PTH fragments in rat organs
CK activity was measured in rat organs 4 h after injection of 0.875 μg of
hPTH(25-39) or hPTH(34-47) or 1.25 μg of hPTH(28-48). Experimental details
are as described for FIG. 16. $P < 0.06$ versus control

| Ex. | Comp. ex. | PTH fragment | CK specific activity (μmol/min per mg of protein) | | |
|---|---|---|---|---|---|
| | | | Epiphysis | Diaphysis | Kidney |
| | 21 | None | 15.0 ± 2.2 | 26.0 ± 3.,9 | 1.43 ± 0.20 |
| 32 | | hPTH(25-39) | 24.0 ± 3.2* | 41.8 ± 4.9* | 3.22 ± 0.78* |
| 33 | | hPTH(28-48) | 20.9 ± 3.0* | 37.2 ± 3.3* | 2.26 ± 0.34* |
| | 22 | hPTH(34-47) | 16.7 ± 2.5 | 24.9 ± 4.8 | 1.64 ± 0.32 |

TABLE 6

Stimulation of DNA synthesis by PTH fragments in rat organs
DNA synthesis was measured in rat organs from 22–24 h after injection of
3.5 μg of bPTH(1-84) or 0.876 μg of hPTH(25-39), 1.25 μg f hPTH(28-48)
or 0.875 μg of hPTH(34-47). Experimental details are as given for FIG. 12.
*$P < 0.05$. **$P < 0.01$ versus central.

| Ex. | Comp. ex. | PTH fragment | [$^3$H]thymidine incorporation into DNA (c.p.m./pg of DNA) | | |
|---|---|---|---|---|---|
| | | | Epiphysis | Diaphysis | Kidney |
| | 23 | None | 25.8 ± 5.2 | 24.1 ± 3.8 | 9.0 ± 2.1 |
| | 24 | bPTH(1-84) | 40.7 ± 3.3** | 43.4 ± 4.7** | 11.8 ± 2.4 |
| 34 | | hPTM(25-39) | 48.4 ± 6.6* | 44.8 ± 4.5** | 11.2 ± 1.9 |
| 35 | | hPTH(28-48) | 46.7 ± 7.4* | 39.1 ± 8.1* | 11.2 ± 2.7 |
| | 25 | hPTH(34-47) | 28.0 ± 7.2 | 28.6 ± 4.2 | 9.0 ± 1.9 |

The invention relates also to pharmaceutical dosage unit forms for systemic (parenteral) administration, which are useful for the mitogenic and bone growth effect in mammals. The term "dosage unit form" as used in this specification and in the claims refers to physically discrete units suitable as unitary dosages for mammalian subjects, each unit containing a predetermined quantity of the essential active ingredient, i.e., a modified PTH, calculated to produce the desired effect in combination with the required pharmaceutical means which adapt said ingredient for systemic administration. Examples of dosage unit forms in accordance with this invention are sterile preparations in liquid vehicles for parenteral administration and sterile dry preparations for the extemporaneous preparation of sterile injectable preparations in a liquid vehicle. Carriers or vehicles include vegetable oils, water, ethanol and polyols, for example, glycerol, propylene glycol, liquid polyethylene glycol, and the like. Liquid pharmaceutical preparations for parenteral administration prepared in water or aqueous solutions advantageously contain suspending agents, such as for example, sodium carboxymethylcellulose and the like. They must be sterile and must be fluid to the extent that easy syringeability exists. Parenteral preparations must also be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example, sugars or sodium chloride. any solid preparations for subsequent extemporaneous preparation of sterile injectable preparations are sterilized, preferably by exposure to a sterilizing gas, such as for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.001 mg. to about 1000 mg. of the essential active ingredient [modified PTH as described herein] per dosage unit form. The amount of the essential active ingredient provided in the pharmaceutical dosage unit forms is based on our calculations that the effective amount of modified PTH for obtaining the desired therapeutic effect in mammals is within a range from about 0.001 mg. per kg. to about 25 mg. per kg. of body weight of the recipient, daily. Preferably 0.5 mg./kg. to about 5 mg/kg. daily is provided.

Certain derivative compounds of the modified PTH may also possess the biological activity associated with the modified PTH and their use is within the scope of the invention. Representative of such derivative compounds are the acylate derivatives, i.e.; compounds where one or more of the hydroxyl, amino and/or imino groups on the molecule of the modified PTH are acylated. Acylation of the hydroxyl, amino or imino groups, including the N-terminal amino group may be carried out by conventional and well-known techniques. For example, by reacting the hydroxyl, amino or imino groups of the compounds (i) with an acylating agent such as an acyl halide of the formula:

 (XI)

wherein Z represents halogen such as chlorine, bromine and iodine and

is a carboxylic acid acyl radical, advantageously a hydrocarbon carboxylic acid acyl of not more than 18 carbon atoms; or a halo-, nitro-, hydroxy-, amino-, cyano-, thiocyano-, or lower alkoxy-substituted hydrocarbon carboxylic acid acyl radical advantageously of not ore than 18 carbon atoms. Representative of carboxylic acid acyl radicals are the acyl radicals of the following acids:

(a) saturated or unsaturated, straight or branched chain aliphatic carboxylic acids, for example acetic, propionic, butyric, isobutyric, tert-butylacetic, valeric, isovaleric, caproic, caprylic, succinic, decanoic, dodecanoic, lauric, tradecanoic, myristic, pentadecanoic, palmitic, margaric, stearic, acrylic, crotonic, undecylenic, oleic, hexynoic, heptynoic, octynoic acids, and the like;

(b) saturated or unsaturated, alicyclic carboxylic acids, for example, cyclobutanecarboxylic acid, cyclopentanecarboxylic acid, methylcyclopentenecarboxylic acid, cyclohexanecarboxylic 5-phenylsalicyclic, 3-methylglutaric, orthosulfobenzoic, cyclohexanesulfamic, cyclopentanepropionic, 1,3-cyclohexanedicarboxylic, 4-cyclohexenecarboxylic, octadecenylsuccinic, octenylsuccinic, methanesulfonic, benzenesulfonic, helianthic, Reinecke's, azobenzenesulfonic, octadecylsulfuric, picric and like acids. Conversely, the free base of the modified PTH is obtained from the corresponding salt, for example from the hydrochloride or sulfate salt, by dissolving or suspending the salt in buffer at about pH 5 to 7, preferably about pH 6, extracting with an immiscible organic solvent, for example chloroform, drying the extract, for example with anhydrous sodium sulfate, and removing the solvent by evaporation.

Acid addition salts of the modified PTH according to the invention may be used to upgrade the free bases, namely, by making acid addition salts of the free bases, subjecting them to purification procedures and then converting the salts back to the free bases by neutralizing with an alkali or contacting with an anionic resin, advantageously to about pH 7.5 to 8.5.

The pharmaceutically acceptable acid addition salts may be used for the same purposes as the free base. Illustrative of pharmaceutically acceptable acid addition salts are those formed upon reaction of the modified PTH with hydrochloric acid, hydrobromic acid, sulfuric acid, phosphoric acid, acetic acid, lactic acid, citric acid, succinic acid, benzoic acid, salicylic acid, pamoic acid, cyclohexanesulfamic acid and the like.

EXAMPLE 36

PARENTERAL AQUEOUS SUSPENSION

A sterile aqueous suspension for parenteral administration containing 0.5 mg. of hPTH (28-48) in each 1 ml. is prepared from the following types and amounts of ingredients.

| hPTH (28-48) | 0.5 gm |
| polysorbate 80 | 8 gms |
| sodium chloride | 18 gms |
| Benzyl alcohol | 18 gms |
| water for injection q.s. | 1000 ml. |

A dose of 1–10 ml. administered subcutaneously to a mammal is useful for mitogenic effect. Similarly, repeating the above procedure but replacing the hPTH (28-48) as used therein with an equal weight of any other PTH modified as described above a therapeutic composition of the invention is obtained and used.

We claim:

1. A method of promoting bone growth in a mammal, which comprises:
   administering systemically to the mammal an effective amount for mitogenesis, of a parathyroid hormone selected from the group consisting of:
   pPTH, bPTH and hPTH, each modified by deletion of the N-terminus and the C-terminus thereof and each comprising amino acid residues +28 to +34.

2. The method of claim 1 wherein the hormone selected is one of bPTH and hPTH.

3. The method of claim 1 wherein the hormone selected comprises amino acid residues +20 to +48.

4. The method of claim 1 wherein the hormone selected is bPTH comprising amino acid residues +3 to +34.

5. The method of claim 1 wherein the hormone selected is hPTH comprising amino acid residues +28 to +48.

* * * * *

UNITED STATES PATENT AND TRADEMARK OFFICE
CERTIFICATE OF CORRECTION

PATENT NO. : 5,457,092

DATED : October 10, 1995

INVENTOR(S) : Klaus-Dieter Schlutter, Hubert Mayer and Edgar Wingender

It is certified that error appears in the above-indentified patent and that said Letters Patent is hereby corrected as shown below:

```
Col. 1, line 45; "Calcifo" should read -- Calcif. --
Col. 2, line 39; "Student's T" should read -- Student's ƒ --
Col. 2, line 58; "P<0.01" should read -- *P<0.01 --
Col. 3, line 21; "T test" should read -- ƒ test --
Col. 4, line 65; "]" should be -- [ --
Col. 7, line 16; "PTH(1'4 34)" should read -- PTH(1-34) --
Col. 8, line 17; "(FIG. 2)" should read -- FIG. 12 --
Col. 10, Table 4, line 1; "cyclic AKP" should read
                -- cyclic AMP --
Col. 11, Table 5, line 1; "CR" should read -- CK --
Col. 11, Table 6, line 11; "hPTM(25-39)" should read
                -- hPTH(25-39) --
Col. 13, line 37; "ore" should read -- more --
```

Signed and Sealed this

Twenty-fifth Day of June, 1996

BRUCE LEHMAN

*Attest:*

*Attesting Officer*  *Commissioner of Patents and Trademarks*